United States Patent [19]

van der Burg

[11] 4,224,321
[45] Sep. 23, 1980

[54] BIOLOGICALLY ACTIVE TETRACYCLIC COMPOUNDS AND PHARMACEUTICAL COMPOSITIONS CONTAINING SAME

[75] Inventor: Willem J. van der Burg, Heesch, Netherlands

[73] Assignee: Akzona Incorporated, Asheville, N.C.

[21] Appl. No.: 835,972

[22] Filed: Sep. 23, 1977

[30] Foreign Application Priority Data

Feb. 10, 1976 [NL] Netherlands .................. 7610942

[51] Int. Cl.³ .................. A61K 31/55; C07D 243/10
[52] U.S. Cl. .................. 424/244; 260/239 BC; 260/333; 260/239 D
[58] Field of Search .................. 260/239 DD, 239 BC, 260/239 D; 424/244

[56] References Cited

U.S. PATENT DOCUMENTS

| | | | |
|---|---|---|---|
| 3,465,042 | 9/1969 | Hardtmann et al. | 424/244 |
| 3,534,041 | 10/1970 | Van Der Burg et al. | 260/239 D |
| 3,600,392 | 8/1971 | Zust et al. | 260/239 BC |
| 3,892,695 | 7/1975 | van der Burg | 260/239 DD |

*Primary Examiner*—Douglas G. Daus
*Assistant Examiner*—D. B. Springer
*Attorney, Agent, or Firm*—Robert H. Falk; Charles A. Wendel; Francis W. Young

[57] ABSTRACT

Novel and biologically active tetracyclic compounds are disclosed of the formula:

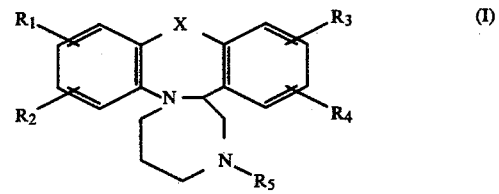

or a pharmaceutically acceptable non-toxic salt thereof, wherein $R_1$, $R_2$, $R_3$, and $R_4$ are each hydrogen, hydroxy, $C_1$-$C_6$ alkyl, $C_1$-$C_6$ alkoxy, $C_1$-$C_6$ alkylthio, halogen, or trifluoromethyl; $R_5$ is hydrogen or $C_1$-$C_6$ alkyl; and X is oxygen or methylene. Pharmaceutical compositions containing these compounds are disclosed to take advantage of CNS-inhibiting properties thereof, especially sedative and tranquillizing properties.

27 Claims, No Drawings

BIOLOGICALLY ACTIVE TETRACYCLIC COMPOUNDS AND PHARMACEUTICAL COMPOSITIONS CONTAINING SAME

BACKGROUND OF THE INVENTION

The invention described and claimed herein relates to the field of biologically active tetracyclic compounds, and the subfields for methods of preparing such compounds, and pharmaceutical compositions containing these tetracyclic compounds.

Corresponding 1,4-di-aza-cyclohexane compounds are known and are described in U.S. Pat. No. 3,534,041 and U.S. Pat. No. 3,701,778. However, they are characterized by possessing CNS-stimulating activity rather than CNS-inhibiting activity, in addition to pronounced antihistamine and anti-serotonin activity. Hence, one skilled in the art would, without experimentation, have expected the novel compounds (I) described below to have similar properties.

SUMMARY OF THE INVENTION

Novel and biologically active tetracyclic compounds are disclosed of the formula

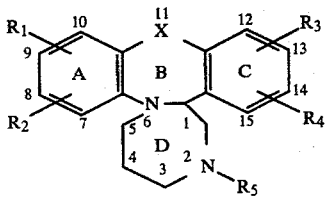

(I)

or a pharmaceutically acceptable non-toxic salt thereof, wherein:

$R_1$, $R_2$, $R_3$, and $R_4$ are each selected from the group consisting of hydrogen, hydroxy, $C_1$-$C_6$ alkyl, $C_1$-$C_6$ alkoxy, $C_1$-$C_6$ alkylthio, halogen, or trifluoromethyl; $R_5$ is selected from the group consisting of hydrogen or $C_1$-$C_6$ alkyl; and X is selected from the group consisting of methylene and oxygen.

These 1,4-diazepine derivatives according to the general formula (I) possess unexpected and surprisingly valuable CNS-inhibiting properties, in particular tranquillizing, sedative and hypnotic activity. Notably, these CNS-inhibiting properties are accentuated by the pronounced hypothermic effect observed with the compounds referred to below. Compared with the aforesaid prior art compounds, the compounds of the general formula (I) show furthermore a dissociation between the antihistamine and antiserotonin activity in favour of the antihistamine activity.

Preferably the benzo groups of the compounds of general formula (I) are unsubstituted ($R_1$ through $R_4$ are hydrogen) or are mono-substituted, whereby the positions 8 and 14 are to be preferred. Likewise, it is desired that $R_5$ be hydrogen or methyl. The notations A, B, C, and D denote the four rings found in the compounds of the invention; ring D is the "diazepine" ring, while rings A and C are pertinent to ring B, the dibenzazepino (if X is methylene) or dibenzoxazepine (if X is oxygen) ring.

The compounds of formula (I) can be prepared in a variety of ways that will be described herein.

One method involves the reduction of the oxo group(s) present in a compound of general formula (II):

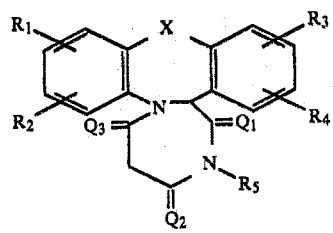

(II)

wherein $Q_1$, $Q_2$, $Q_3$ each are selected from the group consisting of hydrogen (i.e., two hydrogens attached to the ring) or oxygen, with the proviso that at least one of the groups $Q_1$, $Q_2$, and $Q_3$ represents an oxygen doubly bonded to the ring and X, $R_1$, $R_2$, $R_3$, $R_4$, and $R_5$ possess the meanings given above in the previous formula. Such a reduction is carried out in the usual way and under the conditions usual for the reduction of an amide group known to those skilled in the art. Suitable reducing agents in this process are in particular diborane or complex-metal hydrides, such as diisobutylaluminium hydride, and most preferably lithium aluminium hydride.

A second readily utilizable method for the preparation of the compounds of formula (I) consists of the ring closure of a compound with the general formula (IV):

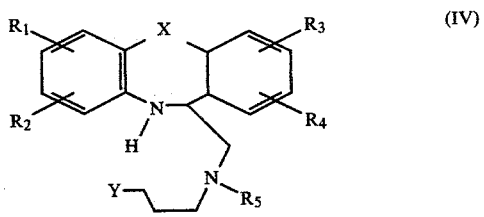

(IV)

or a pharmaceutically acceptable salt thereof, wherein $R_1$, $R_2$, $R_3$, $R_4$, $R_5$, and X have the meanings previously assigned in formula (I), and Y is selected from the group consisting of the halogens, hydroxy ("free hydroxy group"), etherified hydroxy, for example, alkoxy of one to about six carbons, and esterified hydroxy, for example, an acyloxy of one to about six carbons, such as acetoxy. The halogens and the free hydroxy groups are preferred values of Y in this reaction. This ring closure reaction, which is known to those skilled in the art, is preferably carried out in a non-polar solvent, such as toluene or xylene, or in an aprotic polar solvent, such as dimethylsulphoxide, dimethylformamide or acetonitril, and at an elevated temperature which is preferably on or slightly below the boiling point of the solvent.

When Y represents a halogen, the ring closure is facilitated by the presence of a base, such as pyridine or triethylamine, to remove the hydrogen-halide formed during the reaction. On the other hand, if Y is hydroxy, esterified hydroxy or etherified hydroxy, the reaction is preferably performed in the presence of an acid (including a Lewis acid) such as trifluoro-acetic acid, sulphuric acid, phosphoric acid, phosphorus pentoxide, polyphosphoric acid, phosphorus oxychloride, polyphosphoric acid ester, boron trifluoride, aluminium trichloride, and their equivalents to those skilled in the art.

A variant of the above-mentioned method, which will be explained below (without claiming it separately) consists of the reaction of a diamine or an acid addition salt thereof of the general formula (III)

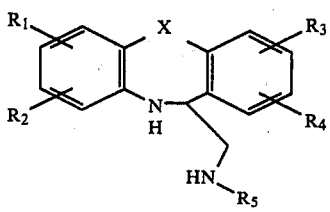
(III)

wherein $R_1$, $R_2$, $R_3$, $R_4$, $R_5$, and X possess the meanings given above in the previous formula (I), with 1,3-dihalopropane, whereby each of the two halogens are selected from the group consisting of fluorine, chlorine, bromine, and iodine. The two halogens, as will be appreciated by those skilled in the art, may be the same or different. Preferably, the halogens are bromine or chlorine. Condensation is carried out in the way usual for such a condensation of a diamine with a dihalo compound known to those skilled in the art. The condensation may be carried out in any suitable solvent, whereby aprotic polar solvents, such as dimethylsulfoxide, dimethylformamide or acetonitril are preferred, but may also be performed in the absence of a solvent, which means that dihalo-propane is used as reagent and solvent as well.

Although this reaction is carried out as a one-step condensation, it actually proceeds in two steps. In the first step 1,3-dihalo-propane reacts with the most alkaline nitrogen (viz. nitrogen in the side-chain) to obtain, as an intermediate compound, a compound of the formula IV, in which Y is halogen.

A third method which is suitable for the preparation of compounds (I) in which X represents the methylene group, consists of the ring closure of a compound (or a pharmaceutically acceptable salt thereof) of general formula (V):

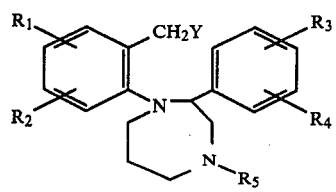
(V)

wherein $R_1$, $R_2$, $R_3$, $R_4$, $R_5$, and Y have the meanings previously assigned. This ring closure takes place at elevated temperature in the presence of an acid (including Lewis acid). Examples of acids, which are suitable for this purpose, have been mentioned already at one of the preceding pages.

The starting materials II, III, IV and V necessary for the preparative methods described above are prepared in ways which are known to those skilled in the art. The starting materials of general formula III are known from the literature (See, for example, U.S. Pat. Nos. 3,534,041 and 3,701,778 already cited, the teachings of which are incorporated herein as if quoted verbatim); while starting materials (II), (IV) and (V) will be discussed below. One or more methods for the preparation of starting materials (II) and (IV) are given schematically on the following page. The starting materials according to general formula (V) are prepared in a way which is fully analogous to the methods taught in published Dutch Patent Application 74.01807 (corresponding to U.S. Pat. No. 4,025,513), the teachings of which are incorporated herein as if copied verbatim.

The preparation of starting materials (II) and (IV) is shown in the following Table.

TABLE

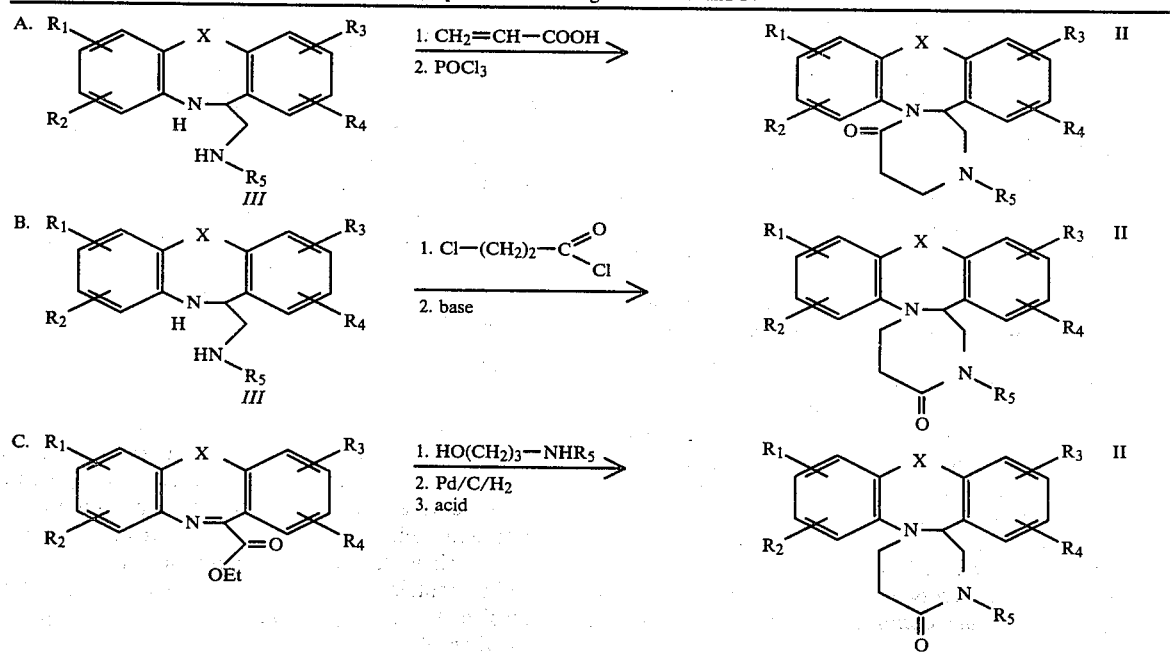

TABLE-continued
Preparation of starting materials II and IV

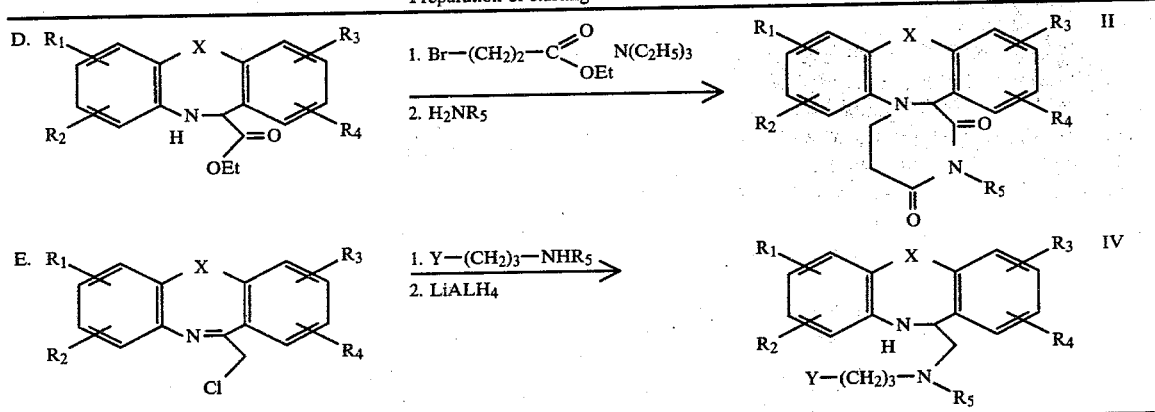

The compounds of the present invention may occur in optically active form as the result of an asymetric carbon atom, so that both optically active end-products are possible, as well as optically inactive end-products. Both the optically inactive form (racemate) and the optically active forms (antipodes) are included amongst the compounds according to the invention. The optically active enantiomers may be obtained by resolving the racemate according to the formula (I) in the usual way with the aid of an optically active acid, for example (+)-tartaric or (−)-tartaric acid. It is also possible to prepare an optically active compound (I) directly, by making use of an optically active starting material, of formula (II), (III), (IV) or (V).

In the compounds according to the invention, a "$C_1$-$C_6$ alkyl group" is understood to mean a straight-chain or branched-chain alkyl group with 1 to 6 carbon atoms, preferably 1 to 4 carbon atoms, such as methyl, ethyl, propyl, isopropyl, butyl, isobutyl, sec. butyl, tert. butyl, or pentyl, isopentyl, neopentyl, hexyl, etc. The alkyl group in the alkoxy and alkylthio groups has the same meaning.

For the compounds of the present invention, halogen is meant to include chlorine, fluorine, bromine, and iodine. The preferred halogens are chlorine and bromine.

The esterified hydroxy group in the definition of Y generally means an acyloxy group of 1 to about 10 carbon atoms. The acyl moiety (of said acyloxy group) is preferably derived from an aliphatic carboxylic (1–6 C) or phenylaliphatic carboxylic (7–10 C) acid, such as acetic acid, propionic acid, butyric acid, pentanoic acid, phenylacetic acid, cinnamic acid or phenyl propionic acid, or from a sulphonic acid such as p-toluene sulphonic acid or methane sulphonic acid.

The etherified hydroxy group used in the definition of Y may in principle be any possible ether moiety. Preferred ether moieties are characterized by the group —OR, in which R is selected from a hydrocarbon radical, (which is optionally substituted by substituents such as halogen, hydroxy, alkoxy or nitro), a heterocyclic radical and a silyl radical. Usual hydrocarbon radicals in this connection are for example alkyl (1–6 C), phenylalkyl (7–10 C), cycloalkyl or cycloalkyl-alkyl (5–10 C) or alkenyl (2–6 C), such as methyl, ethyl, isopropyl, tert. butyl, isobutyl, benzyl, phenylethyl, p-chlorophenyl ethyl, o-nitrophenyl ethyl, cyclohexyl, cyclohexyl methyl or allyl. A well-known heterocyclic ether is the 2-tetrahydropyranyl ether and a well-known silyl ether the trimethylsilyl ether.

By salts of the compounds according to the general formula (I) are understood the non-toxic acid addition salts and quaternary ammonium salts.

The non-toxic acid addition salts according to the invention are prepared in the appropriate way by allowing the free base of formula (I) to react with a pharmaceutically acceptable acid. The usual acids in this connection are: hydrochloric acid, hydrogen bromide or iodide, phosphoric acid, acetic acid, propionic acid, glycollic acid, maleic acid, malonic acid, succinic acid, tartaric acid, citric acid, ascorbic acid, fumaric acid, salicyclic acid and benzoic acid.

The quaternary ammonium salts, and in particular the $C_1$-$C_4$ alkyl quaternary ammonium compounds are obtained by allowing the compounds according to the general formula (I) to react with an alkyl halide, preferably methyl iodide, methyl bromide, or methyl chloride.

It is, of course, possible to introduce or change the substituents in one or both phenyl rings after the reduction/condensation reactions described above. For example, a hydroxy group present may be converted into an alkoxy group and a methoxy group may be converted into a hydroxy group.

The unsubstituted amine according to the general formula (I) ($R_5$=H) may be alkylated in the usual way, for example, by reaction with an alkyl halide. For this purpose, it is however more usual to acylate the nitrogen atom concerned with, for example, an acid chloride or anhydride, and subsequently reduce the keto group of the N-acyl derivative obtained. For the introduction of a methyl group at the nitrogen atom, the Eschweiler-Clarke procedure (warming with a mixture of formaldehyde and formic acid) or the reaction with formaldehyde and sodium cyanoborohydride or the reaction with methylformate and subsequent reduction with $LiALH_4$ are preferably used.

It is also possible to convert the substituted amine according to formula (I) ($R_5 \neq H$) into the corresponding unsubstituted amine ($R_5$=H). A much used method for this purpose consists of the reaction of the alkyl substituted amine (I, $R_5$=alkyl) with an ester of chloroformic acid, followed by hydrolysis.

The compounds according to the invention may be administered by the oral, rectal, and parenteral routes, preferably in a daily dosage of 0.01–10 mg per kg body weight.

When mixed with suitable excipients, such as lactose, starch, magnesium stearate, suppository-mass (fatty acid esters), etc., the compounds may be compressed to give solid dosage forms such as pills, tablets, suppositories or dragees. Optionally mixed with excipients, they may also be made into capsules. With the aid of suitable liquids, for example, water, natural oils, such as soja-bean oil, arachis oil, sunflower seed oil, castor oil, olive oil, etc. the compounds may also be used as injection preparations in the form of solutions, emulsions or suspensions.

In the following examples use is made of the nomenclature given below with respect to the compounds according to general formula I:

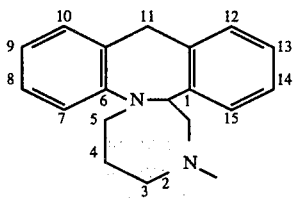

2,3,4,5,11,15b-hexahydro-1H-dibenz[3,4:6,7]azepino[1,2-a](1,4)diazepine

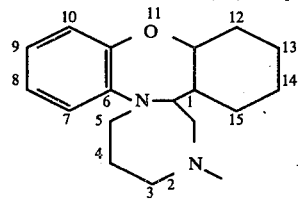

1,2,3,4,5,15b-hexahydro-1,4-diazepino[1,2-d]dibenz[b,f](1,4)oxazepine

EXAMPLES

The following working examples relate to various aspects of the invention as generally described herein and are not intended to restrict the invention to those aspects alone. Alternative techniques can be readily used and the invention should be restricted to the scope of the hereinafter appearing claims.

EXAMPLE I 1,2,3,4,5,15b-hexahydro-2-methyl-1,4-diazepino[1,2-d]dibenz[b,f](1,4)oxazepine.

3.8 g 1,2,3,4,5,15b-hexahydro-2-methyl-5-oxo-1,4-diazepino[1,2-d]dibenz[b,f](1,4)oxazepine, melting point 99°–104° C., is dissolved in 300 ml dry tetrahydrofuran (THF), and diborane gas is subsequently passed through the solution for 1½ hours. The mixture is then boiled under reflux for a further 30 minutes, after which it is cooled and the excess diborane is decomposed by addition of a little 96% ethanol. The mixture is then evaporated to dryness, whereupon 45 ml concentrated hydrochloric acid and 45 ml water are added and the mixture is subsequently heated on a steam bath for 30 minutes. After cooling, the mixture is made alkaline with concentrated ammonia and extracted with ether. The ether layers are washed with water, dried and evaporated to dryness. Yield 1.6 g of an oil; Rf in methanol:acetone (9:1)=0.45 on SiO$_2$.

The product is converted into the hydrochloride by treatment with an alcoholic solution of hydrochloric acid. Melting point of the HCl salt: 220°–222° C.

EXAMPLE II

The following compounds are prepared in a way corresponding to that described in Example I:

2,3,4,5,11,15b-hexahydro-1H-dibenz[3,4:6,7]azepino[1,2-a](1,4)diazepine, melting point 116°–118° C.;

2,3,4,5,11,15b-hexahydro-2-methyl-1H-dibenz[3,4:6,7]azepino[1,2-a](1,4)diazepine, melting point 103°–105° C.;

2,3,4,5,11,15b-hexahydro-9-hydroxy-2-methyl-1H-dibenz[3,4:6,7]azepino[1,2-a](1,4)diazepine(oil), Rf in methanol:acetone (9:1)=0.33 (SiO$_2$);

2,3,4,5,11,15b-hexahydro-2,8-dimethyl-1H-dibenz[3,4:6,7]azepino[1,2-a](1,4)diazepine;

2,3,4,5,11,15b-hexahydro-2,14-dimethyl-1H-dibenz[3,4:6,7]azepino[1,2-a](1,4)diazepine hydrochloride, melting point 223°–226° C.;

1,2,3,4,5,15b-hexahydro-2-methyl-14-methylthio-1,4-diazepino[1,2-d]dibenz[b,f](1,4)oxazepine maleate, melting point 199°–201° C.;

1,2,3,4,5,15b-hexahydro-14-methoxy-2-methyl-1,4-diazepino[1,2-d]dibenz[b,f](1,4)oxazepine maleate, melting point 186°–188° C.;

1,2,3,4,5,15b-hexahydro-2,14-dimethyl-1,4-diazepino[1,2-d]dibenz[b,f](1,4)oxazepino maleate, melting point 170°–172° C.;

1,2,3,4,5,15b-hexahydro-2,12-dimethyl-1,4-diazepino[1,2-d]dibenz[b,f](1,4)oxazepine hydrochloride, 1½ H$_2$O, melting point 235°–237° C.;

1,2,3,4,5,15b-hexahydro-2,12,14-trimethyl-1,4-diazepino[1,2-d]dibenz[b,f](1,4)oxazepine maleate, melting point 192°–195° C.;

1,2,3,4,5,15b-hexahydro-14-chloro-2-methyl-1,4-diazepino[1,2-d]dibenz[b,f](1,4)oxazepine maleate, melting point 171°–173° C.;

1,2,3,4,5,15b-hexahydro-2,8-dimethyl-1,4-diazepino[1,2-d]dibenz[b,f](1,4)oxazepine, (oil) Rf in toluene:ethanol (8:2)=0.42 on SiO$_2$;

2,3,4,5,11,15b-hexahydro-2,14-dimethyl-1H-dibenz[3,4:6,7]azepino[1,2-a](1,4)diazepine.

EXAMPLE III 2,3,4,5,11,15b-hexahydro-1H-dibenz[3,4:6,7]azepino[1,2-a](1,4)diazepine.

A solution of 7.5 g 2,3,4,5,11,15b-hexahydro-3-oxo-1H-dibenz[3,4:6,7]azepino[1,2-a](1,4)diazepine in 200 ml THF is added to a vigorously stirred suspension of 5 g LiALH$_4$ in 400 ml dry THF. The mixture is boiled under reflux for 3 hours, after which it is cooled to about 0° C. 20 ml water is then added slowly to the mixture and the inorganic precipitate which forms is removed by filtration. The filtrate is evaporated to dryness, leaving a crystalline residue. Yield 5.3 g.

Recrystallization from methanol gives a pure product of melting point 117°–119° C.

The compound 1,2,3,4,5,15b-hexahydro-1,4-diazepino[1,2-d]dibenz[b,f](1,4)oxazepine is prepared in a corresponding way.

EXAMPLE IV

The following compounds are prepared by reduction of the corresponding 1-oxo derivatives with lithium aluminium hydride in the way described in example III:

2,3,4,5,11,15b-hexahydro-2-methyl-1H-dibenz[3,4:6,-7]azepino[1,2-a](1,4)diazepine, melting point 103°–105° C.;

1,2,3,4,5,15b-hexahydro-2,14-dimethyl-1,4-diazepino[1,2-d]dibenz[b,f](1,4)oxazepine-maleate, melting point 170°–172° C.;

2,3,4,5,11,15b-hexahydro-8-chloro-2-methyl-1H-dibenz[3,4:6,7]azepino[1,2-a](1,4)diazepine;

1,2,3,4,5,15b-hexahydro-2-methyl-1,4-diazepino[1,2-d]dibenz[b,f](1,4)oxazepine.HCl, melting point 220° C.

EXAMPLE V 2,3,4,5,11,15b-hexahydro-2-methyl-1H-dibenz[3,4:6,-7]azepino[1,2-a](1,4)diazepine.

0.8 g Of the product obtained in example III (melting point 117°–119° C.) is dissolved in 30 ml methyl formate. The solution is heated on a water bath at 40° C. for 20 hours, after which excess methyl formate is removed by evaporation. The resultant crystalline residue is recrystallized from ethanol, giving 0.4 g 2,3,4,5,11,15b-hexahydro-2-formyl-1H-dibenz[3,4:6,-7]azepino[1,2-a](1,4)diazepine of melting point 146°–148° C. This formyl derivative is subsequently dissolved in 100 ml THF, and the solution is then added with stirring to a suspension of 1 g LiALH$_4$ in 200 ml dry ether, after which the mixture is boiled under reflux for a further 1 hour. After cooling, 4 ml water is slowly added and the inorganic precipitate formed is removed by filtration. The filtrate is evaporated to dryness under vacuum, giving a crystalline residue which is recrystallized from toluene.

Yield 320 mg; melting point 103°–104° C.

The compounds 2,3,4,5,11,15b-hexahydro-2-propyl-1H-dibenz[3,4:6,-7]azepino[1,2-a](1,4)diazepine and 1,2,3,4,5,15b-hexahydro-2-propyl-1,4-diazepino[1,2-d]dibenz[b,f](1,4)oxazepine are prepared in a corresponding way by replacing methyl formate by propionyl chloride and an equimolar quantity of triethylamine.

EXAMPLE VI 2,3,4,5,11,15b-hexahydro-2-methyl-1H-dibenz[3,4:6,-7]azepino[1,2-a](1,4)diazepine.

4.76 g 5,6-dihydro-6-methylaminomethyl-11H-dibenzo[b,e]azepine is dissolved in 125 ml dibromopropane and 5 ml triethylamine is added to the solution. The mixture is boiled under reflux with stirring for 2 hours, after which it is cooled. 150 ml Water is then added and the whole is shaken for a little while, after which the aqueous layer is separated from the dibromopropane layer. The organic layer is subsequently dried over sodium sulphate and evaporated to dryness under vacuum. The residue is further purified chromatographically on a silica gel column with methanol:acetone (9:1) as eluent.

Yield 1.1 g, melting point 101°–103° C.

EXAMPLE VII 1,2,3,4,5,15b-hexahydro-2,12,14-trimethyl-1,4-diazepino[1,2-d]dibenz[b,f](1,4)oxazepine maleate.

A. A solution of 2.7 g 11-chloromethyl-2,4-dimethyl-dibenz[b,f](1,4)oxazepine in 24 ml toluene is added at room temperature with stirring to a solution of 10.9 g γ-methylaminopropanol in 17 ml toluene. The mixture is stirred for 6 hours, after which 10 ml water is added during a 15-minute period. The toluene layer is subsequently separated, washed with water and dried over sodium sulphate. The solution thus obtained is stirred during a 15-minute period into a suspension of 1.4 g LiALH$_4$ in 36 ml dry ether. The mixture is then cooled to about 0° C. After addition of 6 ml water, the mixture is filtered and the filtrate is evaporated to dryness under vacuum. Yield 3.2 g 10,11-dihydro-11-{N-(3-hydroxypropyl)-N-methyl}aminomethyl-2,4-dimethyl-dibenz[b,f](1,4)oxazepine as a colourless oil. Rf in toluene:ethanol (9:1)=0.16 (SiO$_2$).

B. A suspension of 1.5 g Hyflo and 2.9 g P$_2$O$_5$ in 18 ml xylene is warmed to boiling point after which a solution of 0.65 g of the product from A, in 3 ml xylene is added. The mixture is boiled under reflux for 2 hours, after which it is cooled and filtered. The xylene solution is subsequently rendered alkaline with 6 ml 33% NaOH solution, after which the mixture is extracted with toluene. The combined toluene extracts are washed with water until neutral, dried over sodium sulphate and evaporated to dryness. The residue (0.055 g) is subsequently dissolved in 1 ml ethanol to which 0.021 g maleic acid has been added. After addition of a little ether, a precipitate is formed, which is further purified by crystallization from ethanol:ether (1:1). Yield 60 mg; melting point of the maleate salt 192°–193° C. Rf in methyl chloride:methanol (95:5)=0.28 on SiO$_2$.

EXAMPLE VIII

The following compounds are prepared in a way corresponding to that described in example VII:

2,3,4,5,11,15b-hexahydro-2-methyl-1H-dibenz[3,4:6,-7]azepino[1,2-a](1,4)diazepine;

2,3,4,5,11,15b-hexahydro-8-methoxy-2-methyl-1H-dibenz[3,4:6,7]azepino[1,2-a](1,4)diazepine;

1,2,3,4,5,15b-hexahydro-14-methoxy-2-methyl-1,4-diazepino[1,2-d]dibenz[b,f](1,4)oxazepine maleate.

EXAMPLE IX 2,3,4,5,11,15b-hexahydro-2-methyl-1H-dibenz[3,4:6,-7]azepino[1,2-a](1,4)diazepine.

10 ml Concentrated sulphuric acid is added dropwise with stirring to 5.38 g 1-(2-hydroxymethyl)phenyl-4-methyl-2-phenyl-1,4-di-aza-cycloheptane at room temperature. The temperature rises during the addition to 40°–45° C. The whole is subsequently stirred for a further 2 hours until a homogenous reaction mixture has been obtained, and 100 g ice is then added, after which the mixture is rendered alkaline with concentrated ammonia (40 ml). The alkaline phase is extracted with chloroform, and the combined organic phases are dried and evaporated to small bulk. The crude reaction product crystallizes and after separation by filtering it is recrystallized from ethyl acetate. Yield 3.8 g; melting point 102°–103° C.

Reaction of this product with methyl iodide gives the corresponding iodomethylate.

Where in stead of the 2-hydroxymethyl starting compound, the corresponding 2-methoxymethyl or 2-acetoxymethyl starting compound is used, the same end-product is obtained in approximately the same yield.

What is claimed is:

1. A compound of the formula

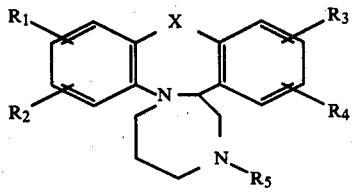

or a pharmaceutically acceptable non-toxic salt thereof, wherein
$R_1$, $R_2$, $R_3$, and $R_4$ are each hydrogen, hydroxy, $C_1$-$C_6$ alkyl, $C_1$-$C_6$ alkoxy, $C_1$-$C_6$ alkylthio, halogen, or trifluoromethyl;
$R_5$ is hydrogen or $C_1$-$C_6$ alkyl; and
X is methylene.

2. The compound of claim 1 wherein $R_1$, $R_2$, $R_3$, $R_4$, and $R_5$ are hydrogen.

3. The compound of claim 1 wherein $R_1$, $R_2$, $R_3$, and $R_4$ are hydrogen and $R_5$ is methyl.

4. The compound of claim 1 wherein $R_1$ is hydroxy, $R_2$, $R_3$, and $R_4$ are hydrogen, and $R_5$ is methyl.

5. The compound of claim 1 wherein $R_1$, $R_2$, and $R_3$ are hydrogen, and $R_4$ and $R_5$ are methyl.

6. The compound of claim 1 wherein $R_1$, $R_3$, and $R_4$ are hydrogen, $R_2$ is methyl and $R_5$ is methyl.

7. The compound of claim 1 wherein $R_1$, $R_3$, and $R_4$ are hydrogen, $R_2$ is chlorine, and $R_5$ is methyl.

8. The compound of claim 1 wherein $R_1$, $R_2$, $R_3$, and $R_4$ are hydrogen and $R_5$ is propyl.

9. The compound of claim 1 wherein $R_1$ and $R_2$ are hydrogen, and $R_3$, $R_4$, and $R_5$ are methyl.

10. The compound of claim 1 wherein $R_1$, $R_3$, and $R_4$ are hydrogen, $R_5$ is methyl, and $R_2$ is methoxy.

11. The compound of claim 1 wherein $R_1$, $R_2$, and $R_3$ are hydrogen, $R_4$ is methoxy, and $R_5$ is methyl.

12. The compound of claim 1 as a maleate salt.

13. The compound of claim 1 in its hydrochloride form.

14. A pharmaceutical composition having CNS-inhibiting properties comprising:
(A) a CNS-inhibiting effective amount of a compound of the formula

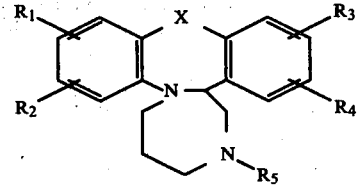

or a pharmaceutically acceptable non-toxic salt thereof wherein
$R_1$, $R_2$, $R_3$ and $R_4$ are each hydrogen, hydroxy, $C_1$-$C_6$ alkyl
$C_1$-$C_6$ alkoxy, $C_1$-$C_6$ alkylthio, halogen, or trifluoromethyl;
$R_5$ is hydrogen or $C_1$-$C_6$ alkyl; and X is methylene; and
(B) a pharmaceutically effective carrier.

15. The composition of claim 14 wherein $R_1$, $R_2$, $R_3$, $R_4$, and $R_5$ are hydrogen.

16. The composition of claim 14 wherein $R_1$, $R_2$, $R_3$, and $R_4$ are hydrogen and $R_5$ is methyl.

17. The composition of claim 14 wherein $R_1$ is hydroxy, $R_2$, $R_3$, and $R_4$ are hydrogen, and $R_5$ is methyl.

18. The composition of claim 14 wherein $R_1$, $R_2$, and $R_3$ are hydrogen, and $R_4$ and $R_5$ are methyl.

19. The composition of claim 14 wherein $R_1$, $R_3$, and $R_4$ are hydrogen, $R_2$ is methyl, and $R_5$ is methyl.

20. The composition of claim 14 wherein $R_1$, $R_3$, and $R_4$ are hydrogen, $R_2$ is chlorine, and $R_5$ is methyl.

21. The composition of claim 14 wherein $R_1$, $R_2$, $R_3$, and $R_4$ are hydrogen and $R_5$ is propyl.

22. The composition of claim 14 wherein $R_1$ and $R_2$ are hydrogen, and $R_3$, $R_4$, and $R_5$ are methyl.

23. The composition of claim 14 wherein $R_1$, $R_3$, and $R_4$ are hydrogen, $R_5$ is methyl, and $R_2$ is methoxy.

24. The composition of claim 14 wherein $R_1$, $R_2$, and $R_3$ are hydrogen, $R_4$ is methoxy, and $R_5$ is methyl.

25. The composition of claim 14 as a maleate salt.

26. The composition of claim 14 in its hydrochloride form.

27. A method for sedation in humans, which comprises administering orally to a human requiring sedation in unit dosage form a pharmaceutical composition comprising:
(A) a pharmaceutically effective sedative amount of a compound of the formula:

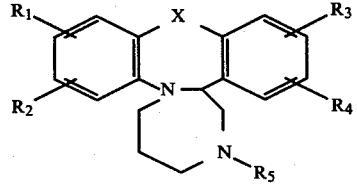

or a pharmaceutically acceptable non-toxic salt thereof,
wherein
$R_1$, $R_2$, $R_3$ and $R_4$ are each hydrogen, hydroxy, $C_1$-$C_6$ alkyl, $C_1$-$C_6$ alkoxy, $C_1$-$C_6$ alkylthio, halogen, or trifluoromethyl;
$R_5$ is hydrogen or $C_1$-$C_6$ alkyl; and
X is methylene; and
(B) a pharmaceutically effective carrier.

* * * * *